(12) United States Patent
Yoshida

(10) Patent No.: US 8,374,890 B2
(45) Date of Patent: Feb. 12, 2013

(54) ELECTRONIC MEDICAL CHART SYSTEM, AND APPARATUS AND METHOD FOR DATA PROCESSING

(75) Inventor: Kazuhiro Yoshida, Chonburi (TH)

(73) Assignee: Canon Kabushiki Kaisha, Tokyo (JP)

( * ) Notice: Subject to any disclaimer, the term of this patent is extended or adjusted under 35 U.S.C. 154(b) by 1124 days.

(21) Appl. No.: 11/694,282

(22) Filed: Mar. 30, 2007

(65) Prior Publication Data
US 2008/0027991 A1    Jan. 31, 2008

(30) Foreign Application Priority Data

Apr. 3, 2006 (JP) ................................. 2006-102289

(51) Int. Cl.
*A61B 5/00* (2006.01)
*G06F 19/00* (2006.01)
(52) U.S. Cl. .......................................................... 705/3
(58) Field of Classification Search .................. 705/2, 3; 345/179
See application file for complete search history.

(56) References Cited

U.S. PATENT DOCUMENTS

| | | | |
|---|---|---|---|
| 5,327,341 A * | 7/1994 | Whalen et al. ..................... 705/3 |
| 6,603,464 B1 * | 8/2003 | Rabin ........................... 345/179 |
| 7,167,166 B1 * | 1/2007 | Burdsall et al. ............... 345/179 |
| 2005/0251422 A1 * | 11/2005 | Wolfman et al. .................. 705/2 |
| 2006/0013484 A1 * | 1/2006 | Kono ............................. 382/181 |
| 2006/0138211 A1 * | 6/2006 | Lubow ........................... 235/375 |
| 2006/0184394 A1 * | 8/2006 | Maughan .......................... 705/3 |
| 2007/0090177 A1 * | 4/2007 | Mitamura ...................... 235/375 |
| 2007/0132744 A1 * | 6/2007 | Burdsall et al. ............... 345/179 |

FOREIGN PATENT DOCUMENTS
JP    2005-141537    6/2005

* cited by examiner

*Primary Examiner* — Gerald J. O'Connor
*Assistant Examiner* — Trang Nguyen
(74) *Attorney, Agent, or Firm* — Fitzpatrick, Cella, Harper & Scinto

(57) ABSTRACT

This invention provides an electronic medical chart system which synchronize medical information on a database with medical information described in a paper medical chart. When data is directly changed by input part other than an electronic pen, a keyboard or the like, a correlation between the paper medical chart and electronic medical chart is released. When a medical record is described in the paper medical chart by the electronic pen, medical record data is reflected in the electronic medical chart based on handwriting data that is described. When the medical record data is directly changed, the correlation between the paper medical chart and electronic medical chart is released, and a new ID is assigned to a reprinted new paper medical chart. When an additional medical record is described in the new paper medical chart again by the electronic pen, the handwriting data is reflected in the electronic medical chart.

18 Claims, 12 Drawing Sheets

ELECTRONIC MEDICAL CHART SYSTEM, AND APPARATUS AND METHOD FOR DATA PROCESSING

BACKGROUND OF THE INVENTION

1. Field of the Invention

The present invention relates to an electronic medical chart system, and an apparatus and method for data processing. More specifically, it relates to an electronic medical chart system that particularly includes: an inputting unit for preparing an electronic medical chart; and an information processor for the electronic medical chart, in accordance with computerization in medicine in hospitals and the like, and corresponding apparatus and method for data processing.

2. Description of the Related Art

Recently, computerization has been advanced in medical use, in hospitals and the like as a result of improvement and the spread of information processing technology. If, in particular, a medical chart, which is the core of medical information, is digitized, it is to be expected that the information can be actively shared between a patient and medical institution, and between medical institutions, and more effective medicine can be realized. However, there is the fact that such digitalization of medical charts has not been advanced as to be expected.

In many electronic medical chart systems, it is troublesome to switch a hand between a keyboard and a mouse during medical practice, difficult to draw an affected part, and impossible to completely input essentially necessary information as the medical chart, and input contents are limited.

Accordingly, in reality, a method is employed in which a doctor or other person in charge inputs contents handwritten in a notebook or paper medical chart, following the medical practice. However, since a predetermined format is generally prepared on a screen for input, there is a problem that input is not allowed without converting and confirming correlation of the item to which the respective contents of handwriting are inputted on a screen.

Additionally, in the electronic medical chart, it is important to ensure security such as protection of personal information (privacy) and prevention of falsifying data.

In order to solve such problems, a hand-writing electronic medical chart system has already been proposed that detects handwriting data representing a time change of a coordinate of a pen point on a medical voucher (medical chart) to prepare the electronic medical chart by text recognition based on the handwriting data (see, for example, Japanese Patent Laid-open No. 2005-141537).

In a constructing system of an electronic medical chart disclosed in Japanese Patent Laid-open No. 2005-141537, a written medical chart is prepared by entering necessary items in a medical chart constituted by digital paper with an electronic pen, with which inputting and reading of texts is possible, and data input in the electronic medical chart is made based on the entries in the written medical chart. The written medical chart is housed in a managing archive so as to be retrieved at random, and the electronic medical chart data is stored in a storage unit for data storage.

FIG. 1 is a schematic diagram of a conventional electronic chart system using the electronic pen. The conventional electronic system includes: an electronic pen 10; a paper medical chart 20 in which a medical record is described by the electronic pen 10; and an electronic medical chart server 30 for receiving handwriting data of the medical record that is described in the paper medical chart 20 by the electronic pen 10. Additionally, it further includes an electronic medical chart 40 in which data is inputted based on the handwriting data from the electronic medical chart server 30.

In the conventional electronic medical chart system, correlating the paper medical chart 20 with the electronic medical chart 40 is performed by reading a 6×6 dot arrangement pattern printed on the paper medical chart, identifying an ID of the paper medical chart and position of the handwriting, and recording them in the corresponding electronic medical chart.

However, in the above conventional electronic medical chart system, medical information is assumed to be inputted or additionally inputted based on only the handwriting data representing the time change of the coordinate of the pen point on the paper medical chart. Accordingly, when the medical information is inputted with input means other than the handwriting data, for example, a keyboard or mouse of a PC, a data content of the information described in the paper medical chart does not coincide with a data content of the digitalized medical information.

FIG. 2 is an explanatory diagram of operation of the conventional electronic medical chart shown in FIG. 1. Moreover, the left side of FIG. 2 shows a flow regarding the paper medical chart 20, and the right side thereof shows a flow regarding the electronic medical chart 40.

First, the medical record is described in the paper medical chart 20 by the electronic pen 10 (Step a), and then medical record data is reflected in the electronic medical chart 40 based on the handwriting data that is recorded by the electronic pen 10 (Step b). Further, an additional medical record is described in the paper medical chart 20 by the electronic pen 10 (Step c), and then the handwriting data is reflected in the electronic medical chart 40 (Step d). These steps are basically repeated. However, if the handwriting data is attempted to be reflected in the electronic medical chart 40 (Step g) in the case where the medical record data is directly changed in the electronic medical chart 40 (Step e) and an additional medical record is further described in the paper medical chart 20 (Step f), there arises a difference between the medical record on the paper medical chart 20 and the medical record data recorded on the electronic medical chart 40. Accordingly, there arises a difference between the described contents.

The problem is not only limited to the electronic medical chart system but also to a system for changing electronic data via the two input means, electronic pen and keyboard of the PC.

SUMMARY OF THE INVENTION

The present invention was made in view of such problems, and it is an object of the present invention to provide an electronic medical chart system, and an apparatus and method for data processing, which can completely synchronize (make coincide) medical information on a database with medical information described in a paper medical chart. Additionally, it is an object of the present invention to provide an information processing system capable of synchronizing (making coincide) information, which is entered on paper by an electronic pen, with information on the database in a system in which the information is inputted on the database via two input means, a keyboard of an electronic terminal and the electronic pen.

In order to achieve such objects, the present invention provides an electronic medical chart system for maintaining a medical record, including: a first medical chart in which fine dots are printed on the entire sheet of a form in advance; writing means with which the medical record is entered in the first medical chart to generate medical record data constituted by contents and positional coordinates of the writing; data management means for maintaining the medical record data; correlation means for correlating the first medical chart with the medical record data; data control means for controlling transmission/reception of the medical record data between the writing means and data management means; and data correlation release means for releasing a correlation between the first medical chart and medical record data when the medical record data is changed by writing means other than the writing means for the first medical chart.

Additionally, the first medical chart includes a communications instruction region for issuing an instruction on transmission/reception of the medical record data between the writing means, data management means and data control means with a specific arrangement pattern of the fine dots.

Additionally, data management means and medical chart print means for printing a new second medical chart are included, in which the data management means for warning a user that writing is not allowed and for requesting the user to print the new second medical chart when the medical record is written in the first medical chart after the correlation between the first medical chart and medical record data is released by the data correlation release means.

Additionally, medical chart print means is provided with that prints the new second medical chart immediately after the correlation between the first medical chart and medical record data is released by the data correlation release means.

Additionally, user selection means to release data correlation includes allowing the user to select whether to release the correlation between the first medical chart and medical record data before the correlation between the first medical chart and medical record data when the medical record data is changed by writing means other than the writing means for the first medical chart.

Additionally, the writing means includes: reading means for recognizing the fine dots; conversion means for converting handwriting obtained by entering the medical record in the first medical chart and the positional coordinates in medical record data; and communications means for performing transmission/reception of the medical record data between the data control means and data management means.

Additionally, the conversion means is a processor, and the processor performs image processing on the arrangement pattern of the fine dots recognized by the reading means and has a function for calculating a current position of the writing means.

Additionally, the processor compares images of the arrangement patterns of the dots recognized by the reading means with each other, and has a function for calculating a movement direction and distance of the writing means.

Additionally, an apparatus for data processing of the present invention includes: receiving means for receiving information that is entered on paper by the electronic pen; input means with which information inputted with input means other than the electronic pen is inputted; and data management means for maintaining the information received by the receiving means and information inputted with the input means, and when entering on the paper is made by the electronic pen after the input is made with the input means, a dialogue on printing the information stored in the data management means on paper is displayed.

Additionally, when an instruction on printing is issued in accordance with the display, the information inputted with the input means and information received by the receiving means is allowed to be printed.

Additionally, a method for data processing of the present invention includes the steps of: receiving information that is recorded on paper by an electronic pen; inputting information that is inputted with input means other than the electronic pen; and data management to maintain the information received by the receiving step and information inputted with the input means, and when entering on the paper is made by the electronic pen after the input is made with the input step, a dialogue on printing the information stored in the data management step on paper is displayed.

Additionally, when an instruction on printing is issued in accordance with the display, the information inputted by the inputting step and information received by the receiving step is allowed to be printed.

An electronic medical chart system of the present invention includes: a first medical chart in which fine dots are printed on the entire sheet of a form in advance; writing means with which the medical record is entered in the first medical chart to generate medical record data constituted by contents and positional coordinates of the writing; data management means for maintaining the medical record data; correlation means for correlating the first medical chart with the medical record data; data control means for controlling transmission/reception of the medical record data between the writing means and data management means; and data correlation release means for releasing a correlation between the first medical chart and medical record data when the medical record data is changed by writing means other than the writing means for the first medical chart. Thus, the correlation between the database and an ID of the corresponding medical chart can be released even when the medical information is inputted with input means other than a digital pen, a keyboard and a mouse of a PC, and the like. A new medical chart, to which a new ID is assigned, is printed so that the medical information on the database can be completely synchronized (made to coincide) with the medical information described in the paper medical chart.

Additionally, in the system in which the information is inputted on the database via the two input means, the input part (keyboard, mouse) of the electronic terminal and electronic pen, it becomes possible to synchronize (make coincide) the information, which is recorded on the paper by the electronic pen, with the information on the database.

Further features of the present invention will become apparent from the following description of exemplary embodiments (with reference to the attached drawings).

DESCRIPTION OF THE EMBODIMENTS

Embodiments of the present invention will be described hereinafter with reference to the accompanying drawings.

First Embodiment

Figure 3:
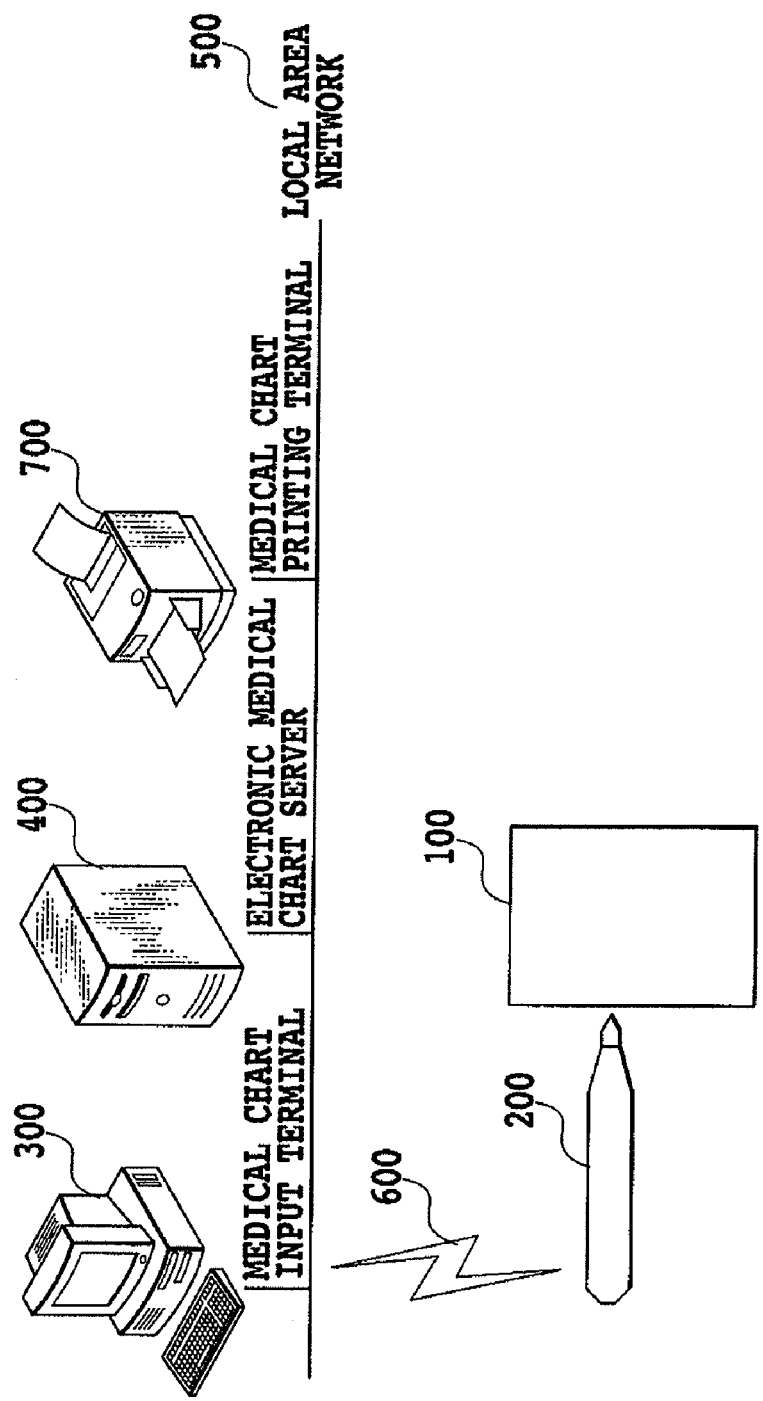
FIG. 3 is a schematic diagram for explaining a first embodiment of an electronic medical chart system of the present invention.

FIG. 3 is a schematic diagram for explaining a first embodiment of an electronic medical chart system of the present invention. The electronic medical chart system according to the first embodiment of the present invention includes: a paper medical chart 100; a digital pen (electronic pen) 200; a medical chart input terminal 300; an electronic medical chart server 400; and a medical chart printing terminal 700, and a local area network 500 enables them to communicate with each other. Additionally, the digital pen 200 transmits medical information described in the paper medical chart 100 by a doctor to the medical chart input terminal 300 via radio communications 600.

Figure 4:
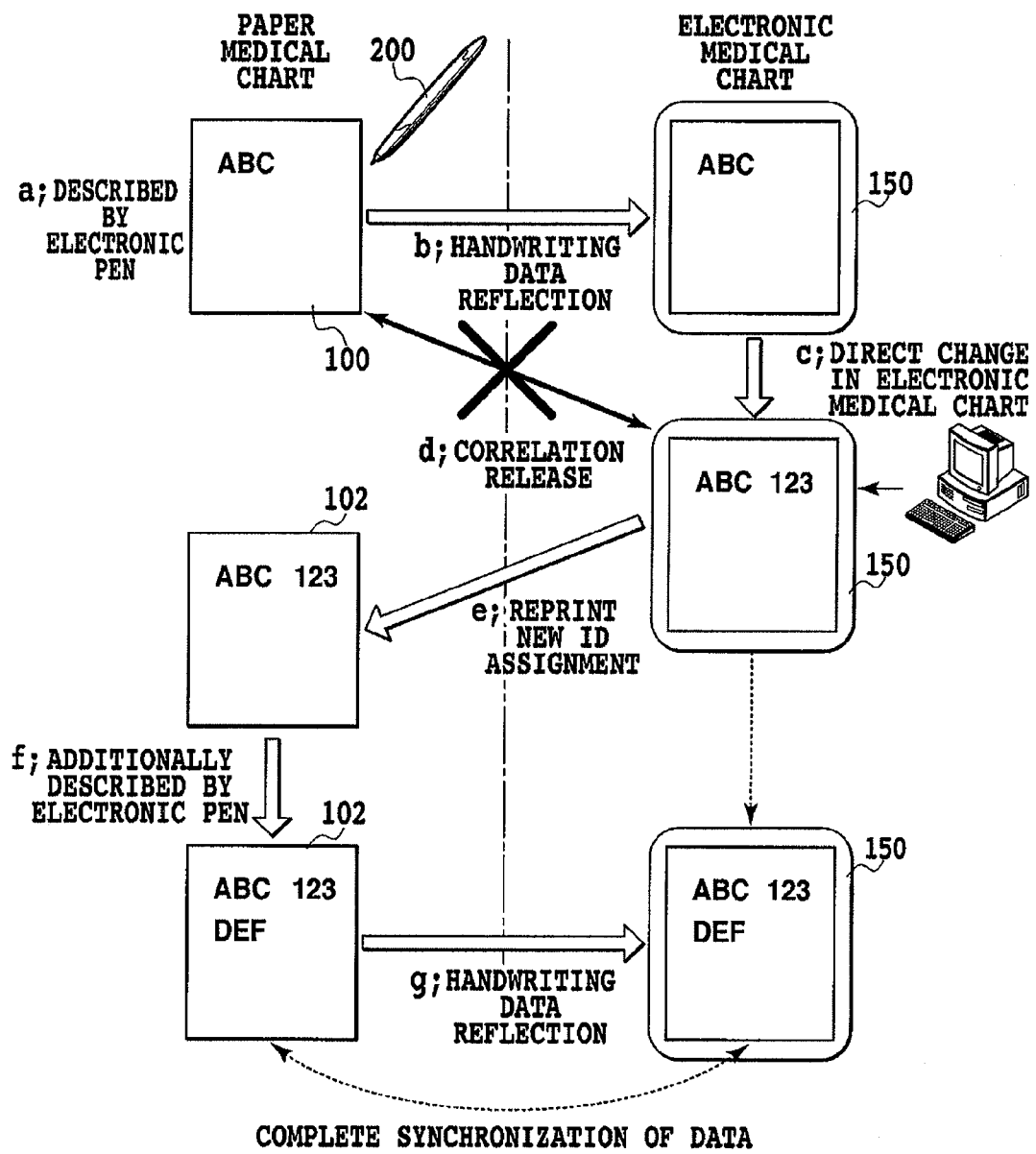
FIG. 4 is an explanatory diagram of operation of the electronic medical chart system of the present invention shown in FIG. 3.

FIG. 4 is an explanatory diagram of operation of the electronic medical chart system of the present invention shown in FIG. 3. In the first embodiment, when data of the electronic medical chart 150 is directly changed by a keyboard of the medical chart input terminal 300, or the like, which is input means other than the electronic pen 200, a correlation between the paper medical chart 100 and electronic medical chart 150 is released. Moreover, the left side of FIG. 4 shows a flow of processing to the paper medical chart 100 of a certain person, and the right side thereof shows a flow of processing to the electronic medical chart 150 stored in the electronic medical chart server in accordance with the paper medical chart of the person.

First, a medical record is described in the paper medical chart 100 by the electronic pen 200 (Step a), and then medical record data is reflected in the electronic medical chart 150 based on handwriting data that is described by the electronic pen 200 (Step b). Thereafter, when the medical record data is directly changed in the electronic medical chart 150 via the keyboard of the medical chart input terminal 300 (Step c), the correlation between the paper medical chart 100 and electronic medical chart 150, which are managed by the electronic medical chart server 400, is released (Step d). Moreover, the release means that the information entered in the paper medical chart 100 is not made to link to the information of the electronic medical chart 150 in the electronic medical chart server 400, and information of the release is recorded in the electronic medical chart server storing the electronic medical chart 150. After the release, information is entered in the paper medical chart 100 related to the release. Thereupon, the medical chart input terminal 300 obtains an ID of the paper medical chart 100 as described below, and checks the release information to the paper medical chart 100 recorded in the electronic medical chart server 400. As a result of the check, the medical chart input terminal 300 recognizes the information that is input as an instruction regarding the paper medical chart 100 in a state of release, and displays, on a displaying part of the paper medical chart input terminal 300, a dialogue on reprinting the data after the medical record date is changed in Step c. In the dialogue, a message is indicated that the electronic medical chart 150 does not synchronize with the paper medical chart 100 and reprinting is necessary. A user (doctor, nurse) prints the changed medical record data with the medical chart printing terminal 700 in accordance with the dialogue. A new ID is assigned to a reprinted new paper medical chart 102 to be printed on the new paper medical chart 102 as an arrangement pattern of fine dots as described below (Step e). Additionally, the ID information is stored and managed in the medical chart input terminal 300 and electronic medical chart server 400. When an additional medical record is described in the new paper medical chart 102, to which the new ID is assigned, by the electronic pen again (Step f), the electronic medical chart input terminal 300 identifies the ID and reflects the handwriting data in the electronic medical chart 150 (Step g). As a result, the medical record on the new paper medical chart 102 completely coincides (synchronizes) with the medical record data recorded on the electronic medical chart 150.

Figure 5:
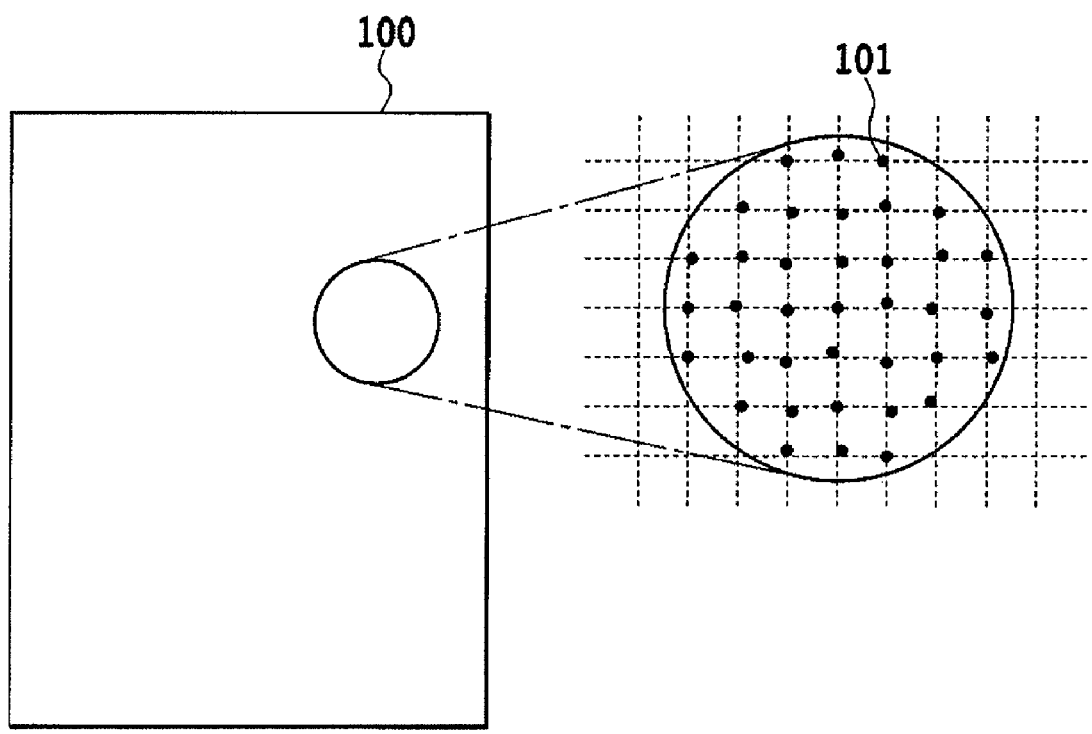
FIG. 5 is an enlarged view of a part of a space of a paper medical chart according to the electronic medical chart system of the present invention.

FIG. 5 is an enlarged view of a part of a space of the paper medical chart according to the electronic medical chart system of the present invention. The paper medical chart 100 is a form on which fine dots 101 are printed in advance at an interval of about 0.3 mm with ink containing carbon. The fine dots 101 are pattern-arranged in a shape of a slightly deformed grid, and an arranged pattern of the fine dots 101 having a specific region of 2 mm square is uniquely printed to all forms each having the printed fine dots 101. A position on the paper medical chart 100 can be identified by recognizing the arrangement pattern of the fine dots 101 having the specific region of 2 mm square.

Additionally, in an arrangement pattern of the fine dots 101 of the paper medical chart 100, a specific arrangement pattern of the fine dots 101 can be printed on every paper medical chart (a specific ID is assigned to every medical chart). Judgement of the arrangement pattern of the fine dots 101 makes it possible to identify to which patient the paper medical chart 100 belongs.

Figure 6:
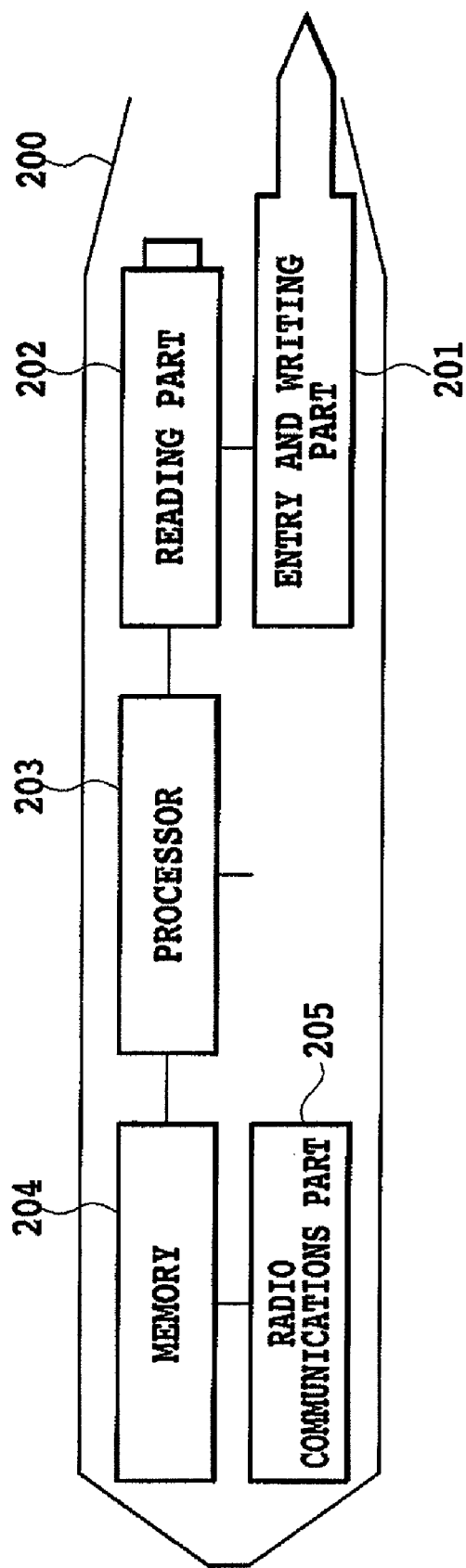
FIG. 6 is a constitutional diagram of a digital pen according to the electronic medical chart system of the present invention.

FIG. 6 is a constitutional diagram of the digital pen according to the electronic medical chart system of the present invention. The digital pen 200 includes: an entry and writing part 201; a reading part 202; a processor 203; a memory 204; and a radio communications part 205, and is a unit with which entering the medical record on the paper medical chart 100, preparing the medical record data, transmitting the medical record data and inputting the medical record data are made.

The entry and writing part 201, similar to a typical entering tool, includes an ink cartridge and pen point so that a track (handwriting) left by the digital pen 200 can be checked visually. Additionally, the reading part 202 is a digital camera for photographing the fine dots 101 with infrared rays approximately 100 times per second, recognizes only the fine dots printed with the ink containing carbon, and does not recognize a printed part of the paper medical chart 100, an ink part entered with the digital pen 200 and the like.

The processor 203 performs image processing on the arrangement pattern of the fine dots 101 photographed by the reading part 202, and successively calculates an accurate current position of the digital pen 200. Further, the processor 203 compares images of the arrangement patterns of the fine dots 101 photographed by the reading part 202 with each other, calculates a movement direction and distance and the like of the digital pen 200, and generates vector data having a SVG (Scalable Vector Graphics) form or the like. Additionally, if a specific text inputting region is set in advance, the handwriting of the digital pen 200 in the specific region can be converted to a text code. The medical record is entered in the paper medical chart 100 with the entry and writing part 201, and the processor 203 digitalizes the position on the paper medical chart 100 and the handwriting of the digital pen 200 with the arrangement patterns of the fine dots 101 photographed at the writing. Thus, all medical records, a personal ID, texts, lines, figures and the like, can be made into data.

The memory 204 temporarily maintains the medical record data generated by the processing by the processor 203 and the read arrangement pattern of the fine dots 101 until receiving an instruction on data transmission via a communications instruction region. Additionally, the memory 204 maintains a program to be processed in the processor 203.

The radio communications part 205 performs the short range radio communications 600 between a personal computer, peripheral unit, digital household appliance and the like, with use of, for example, bluetooth technology. Additionally, the radio communications part 205 performs the radio communications 600 with the medical chart input terminal 300, and transmits the data inputted in the paper medical chart 100 to the medical chart input terminal 300.

The paper medical chart 100, on which the fine dots 101 are printed, and digital pen 200 of the embodiment can be constituted by Anoto paper and Anoto pen (registered trade marks of Anoto AB) proposed by Anoto AB. Additionally, the medical chart input terminal 300 controls communications between the digital pen 200 and electronic medical chart server 400.

Figure 7:
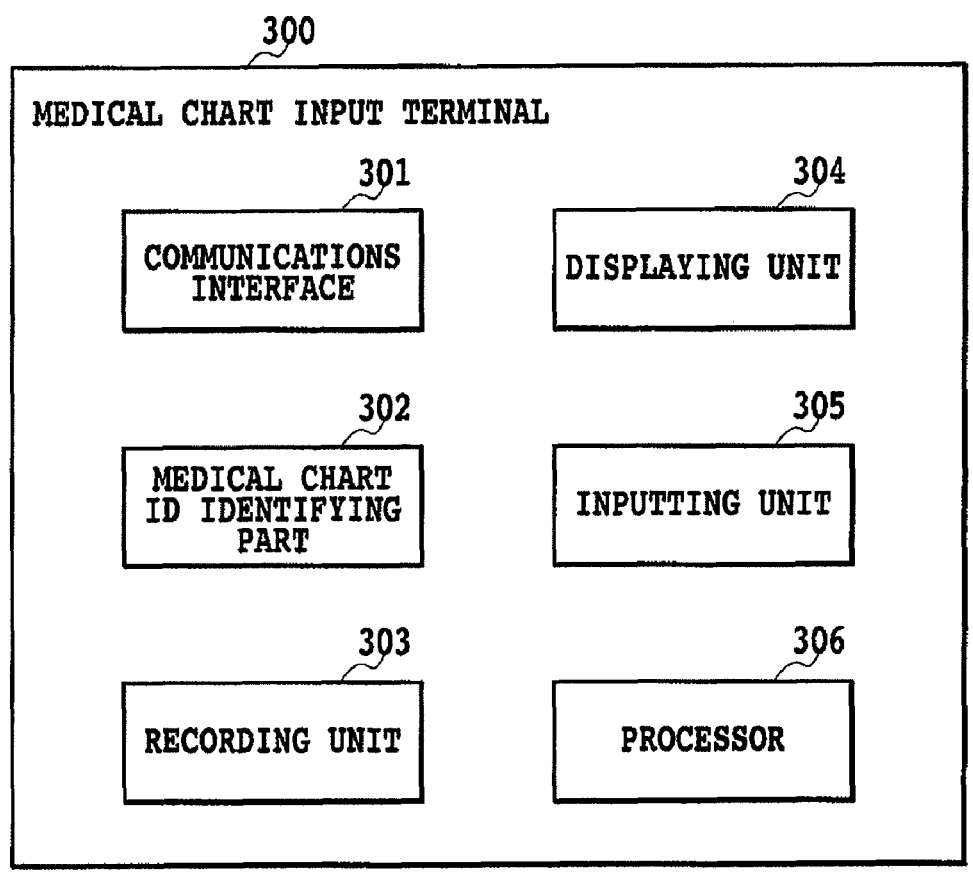
FIG. 7 is a constitutional diagram of a medical chart input terminal according to the electronic medical chart system of the present invention.

FIG. 7 is a constitutional diagram of the medical chart input terminal according to the electronic medical chart system of the embodiment. The medical chart input terminal 300 is a computer system in reality. In terms of hardware, the input terminal 300 includes: a recording unit 303 (magnetic disc, optical disc or the like) for computers for recording information; an inputting unit 305 (keyboard, mouse) with which an instruction is imparted to the computer; a processor 306 for calculating; and a displaying unit 304 such as a CRT for displaying the calculation result. The input terminal 300 further includes: a communications interface 301 communicable with the digital pen 200 and electronic medical chart server 400 via the radio communications 600 and local area network 500; and a medical chart ID identifying part 302 for identifying the ID assigned to the paper medical chart 100.

Additionally, the medical chart input terminal 300 receives the arrangement pattern of the fine dots 101 of the paper medical chart 100 from the digital pen 200 via the radio communications 600.

Additionally, the medical chart ID identifying part 302 of the medical chart input terminal 300 stores all arrangement patterns of the fine dots 101 printed on the paper medical chart 100 in advance, and verifies the stored arrangement pattern of the fine dots 101 with the received arrangement pattern of the fine dots 101 to identify a specific ID owned by the paper medical chart 100. Of course, the electronic medical chart server 400 may store the arrangement patterns to perform verification in accordance with an ID verification request from the medical chart input terminal 300.

Additionally, the medical chart input terminal 300 transmits the handwriting data received from the digital pen 200, specific ID of the paper medical chart 100 identified in the medical chart input terminal 300 and input means information to the electronic medical chart server 400 via the local area network 500.

The displaying unit 304 reads the medical record data maintained by a database 403 described below via the local area network 500 to display the electronic medical chart 150.

Figure 8:
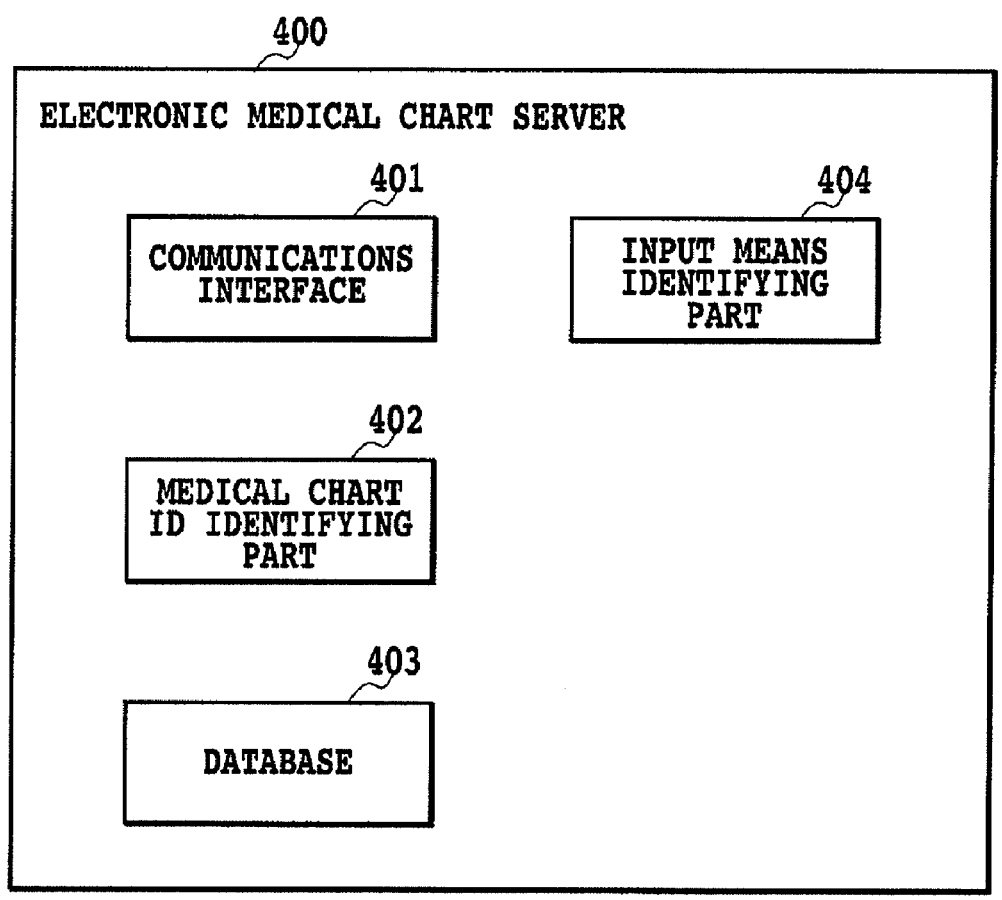
FIG. 8 is a constitutional diagram of an electronic medical chart server according to the electronic medical chart system of the present invention.

FIG. 8 is a constitutional diagram of the electronic medical chart server according to the electronic medical chart system of the present invention. The electronic medical chart server 400 includes: a communications interface 401 communicable with the medical chart input terminal 300 via the local area network 500; a medical chart ID identifying part 402; the database 403; input means identifying part 404 and the like, and maintains and uses the medical record data.

The medical chart ID identifying part 402 verifies the medical chart ID received from the medical chart input terminal 300 with an ID of the medical record data recorded on the database 403. On the database 403, the medical chart ID received from the medical chart input terminal 300 is correlated with the medical record data, and the correlation is stored. The identifying part 402 may or may not store the arrangement pattern of the fine dots 101.

The input means identifying part 404 identifies input means based on the input means information from the medical chart input terminal 300, and notifies the medical chart ID identifying part 402 of input means other than the digital pen 200.

Figure 9:
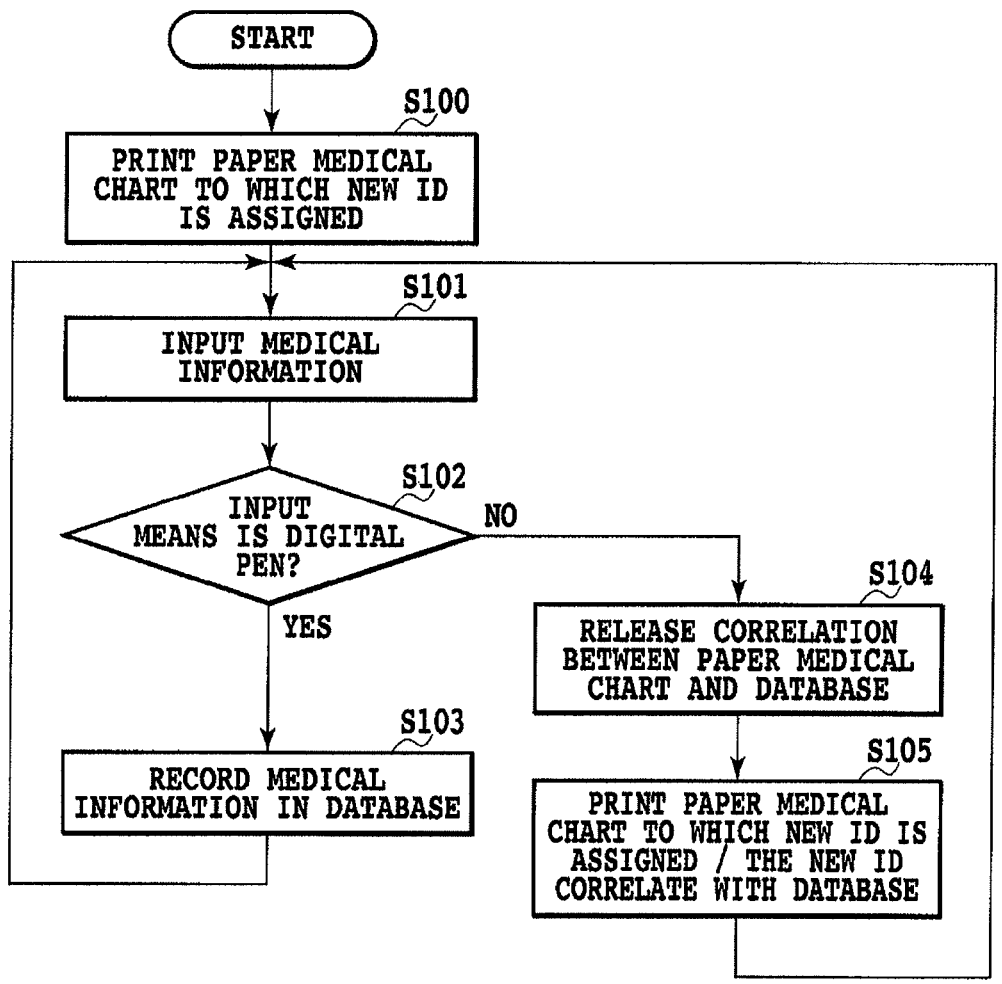
FIG. 9 is a flowchart for explaining the operation of the first embodiment of the electronic medical chart system of the present invention.

FIG. 9 is a flowchart for explaining the operation of the first embodiment of the electronic medical chart system of the present invention. First, in S100, a new ID is assigned to the paper medical chart by the medical chart ID identifying part 402 of the electronic medical chart server 400, and an arrangement pattern based on the new ID is printed from the medical chart printing terminal 700. The printed paper becomes the paper medical chart 100.

Next, in S101, the user inputs the medical information. The input means is either digital pen 200 or inputting unit 305 (keyboard, mouse or the like) of the medical chart input terminal 300. And then, in S102, the input means identifying part 404 of the electronic medical chart server 400 identifies input means of the medical information. If the input means is the digital pen 200, the process proceeds to S103, and if the input means is the inputting unit 305 of the medical chart input terminal 300, the process proceeds to S104.

Next, in S103, the electronic medical chart server 400 records the medical information received via the communications interface 401 on the database 403. And then, in S104, the input means identifying part 404 notifies the medical chart ID identifying part 402 that the input means is not the digital pen 200, and the medical chart ID identifying part 402 makes the correlation between the inputted database and the medical chart ID invalid.

Next, in S105, the medical chart ID identifying part 402 issues a new medical chart ID to correlate the new medical chart ID with the database. In the medical chart printing terminal 700, an arrangement pattern based on the new ID and the recorded medical information are printed on a new medical chart form. Thereafter, a process proceeds to S101.

Second Embodiment

Figure 10:
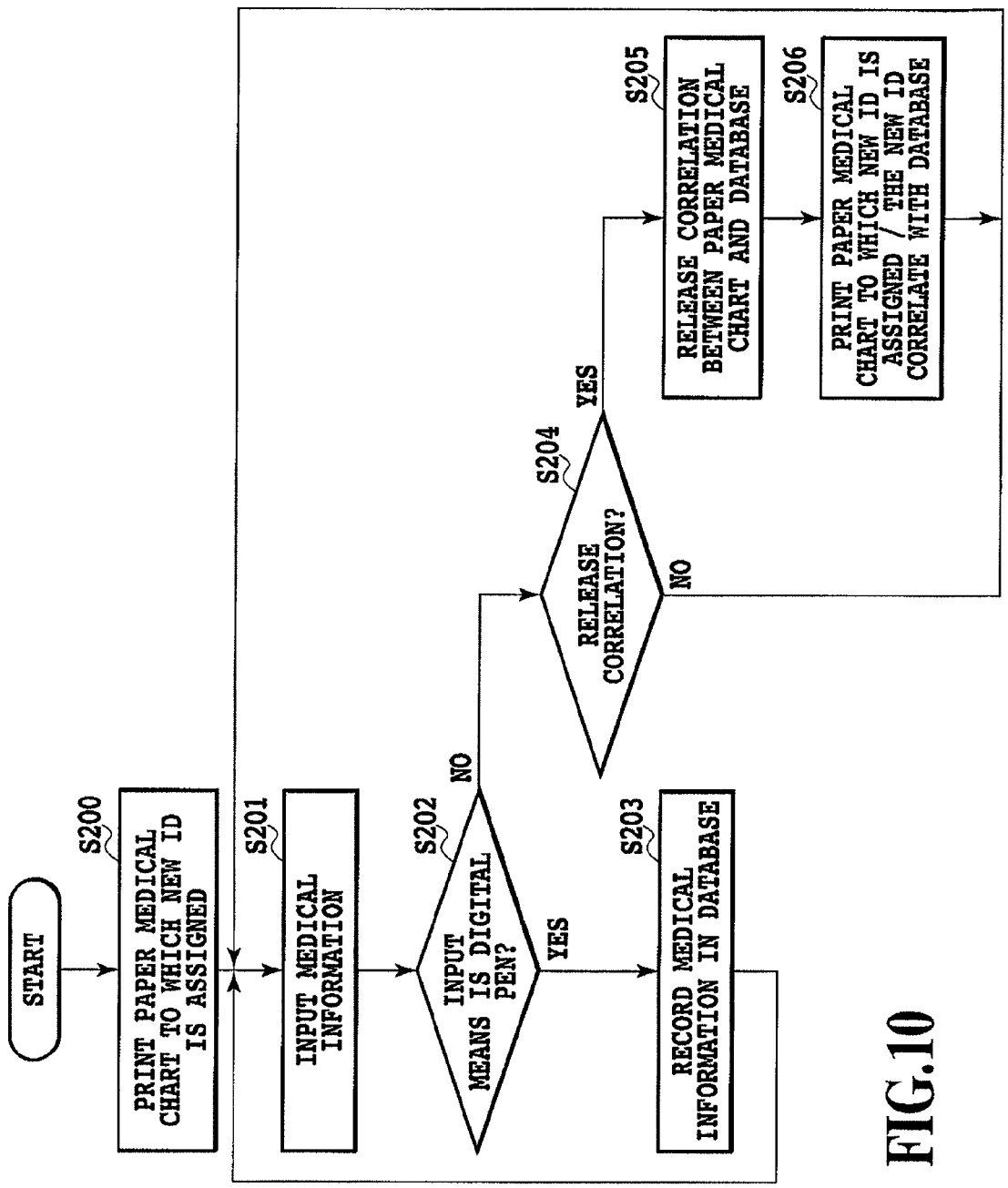
FIG. 10 is a flowchart for explaining operation of a second embodiment of the electronic medical chart system of the present invention.

FIG. 10 is a flowchart for explaining operation of a second embodiment of the electronic medical chart system of the present invention. First, in S200, a new ID is assigned to the paper medical chart by the medical chart ID identifying part 402 of the electronic medical chart server 400, and an arrangement pattern based on the new ID is printed from the medical chart printing terminal 700. The printed form becomes the paper medical chart 100.

Next, in S202, the user inputs the medical information. The input means is either digital pen 200 or inputting unit 305 of the medical chart input terminal 300. Next, in S202, the input means identifying part 404 of the electronic medical chart server 400 identifies the input means of the medical information. A process proceeds to S203 if the input means is the digital pen 200, and a process proceeds to S204 if the input means is the inputting unit 305 of the medical chart input terminal 300.

Next, in S203, the electronic medical chart server 400 records the medical information received via the communications interface 401 on the database 403. Thereafter, a process proceeds to S201.

Next, in S204, the user selects whether to release the correlation between the inputted database and the medical chart ID. In the case where the user selects that the correlation is not released, the process proceeds to S201, and in the case where the user selects that the correlation is released, the process proceeds to S205.

Next, in S205, the input means identifying part 404 notifies the medical chart identifying part 402 that the input means is not the digital pen 200, and the medical chart ID identifying part 402 makes the correlation between the inputted database and the medical chart ID invalid.

Next, in S206, the medical chart ID identifying part 402 issues a new medical chart ID to correlate the new medical chart ID with the database. In the medical chart printing terminal 700, an arrangement pattern based on the new ID and the recorded medical information are printed on a new medical chart form.

Figure 11:
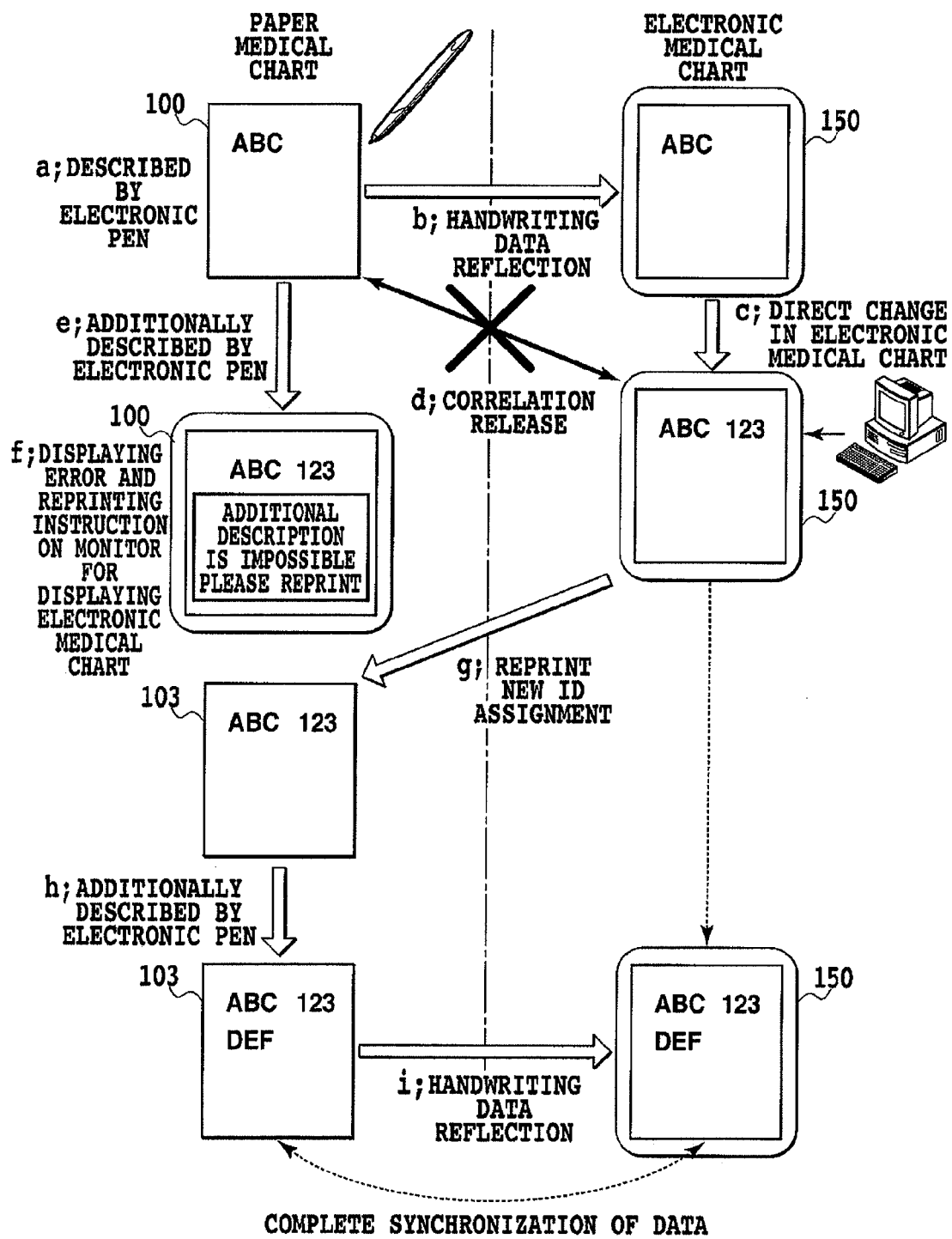
FIG. 11 is an explanatory diagram of the operation of the second embodiment of the electronic medical chart system of the present invention.

FIG. 11 is an explanatory diagram of the operation of the second embodiment of the electronic medical chart system of the present invention. In the second embodiment, when the data of the electronic medical chart 150 is directly changed by the keyboard or the like, which is input means other than the electronic pen 200, the correlation between the paper medical chart 100 and electronic medical chart 150 is released. When additional information is entered in the paper medical chart 100 by the electronic pen 200 after the release, an error message indicating an instruction on reprinting is outputted. Moreover, the left side of FIG. 11 shows a flow of processing to the paper medical chart 100, and the right side thereof shows a flow of processing to the electronic medical chart 150.

First, the medical record is described in the paper medical chart 100 by the electronic pen 200 (Step a), and then the medical record data is reflected in the electronic medical chart 150 based on the handwriting data that is described by the electronic pen 200 (Step b). When the medical record data is directly changed in the electronic medical chart 150 (Step c), the correlation between the paper medical chart 100 and electronic medical chart 150 is released (Step d). When an additional medical record is described in the paper medical chart 100 by the electronic pen 200 after the release (Step e), an error is displayed on a monitor for displaying electronic medical charts (a monitor of the electronic medical chart input terminal 300). When the user (doctor, nurse) sends the instruction on reprinting (Step f), the changed medical record data is reprinted, and a new ID is assigned to a paper medical chart 103 similar to the first embodiment (Step g). When the additional medical record is described in the paper medical chart 103 assigned the new ID by the electronic pen 200 (Step h), the handwriting data is reflected in the electronic medical chart 150 (Step i). Thus, the medical record on the paper medical chart 103 completely coincides (synchronizes) with the medical record data recorded on the electronic medical chart 150.

Third Embodiment

Figure 12:
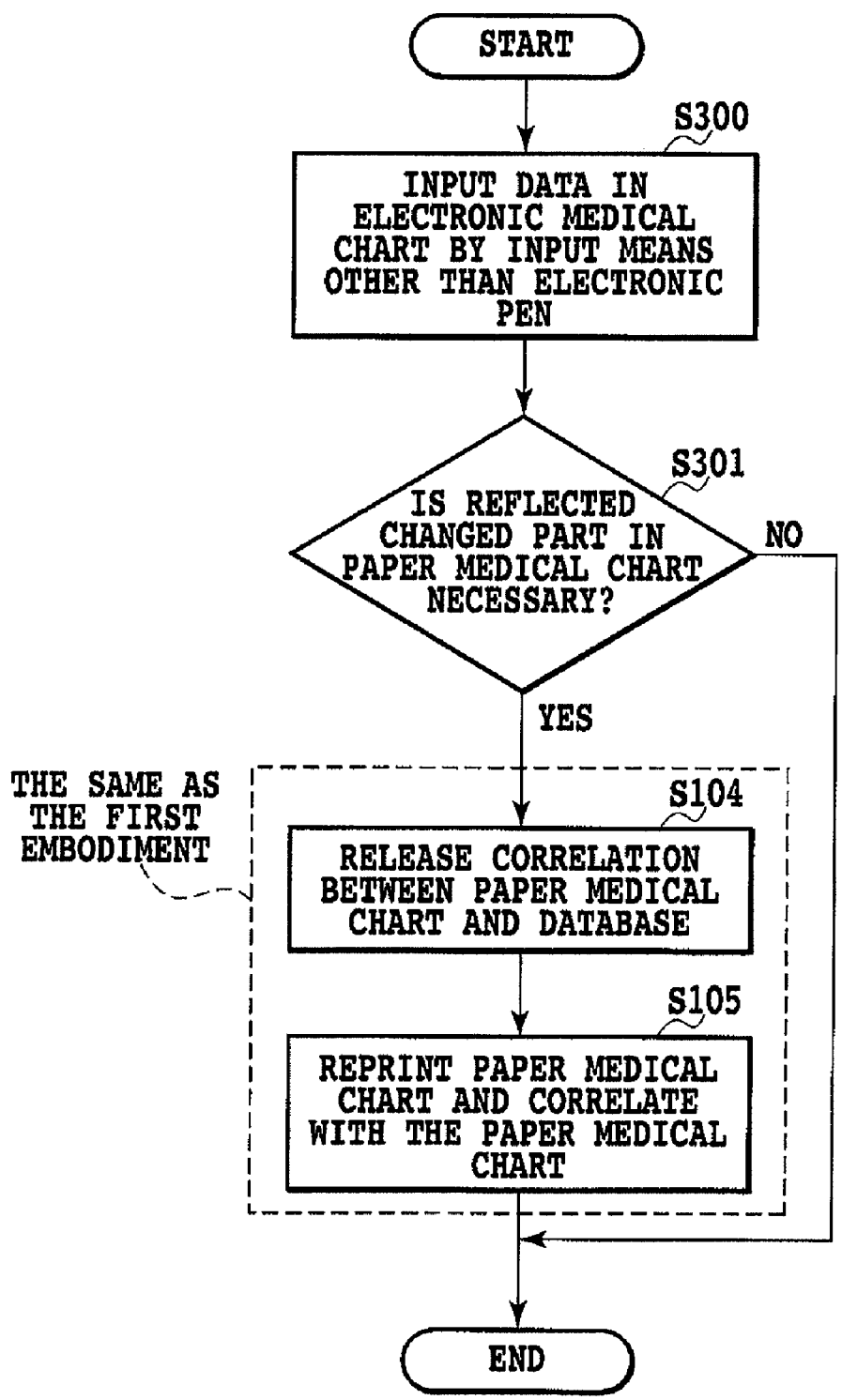
FIG. 12 is a flowchart for explaining operation of a third embodiment of the electronic medical chart system of the present invention.

FIG. 12 is a flowchart for explaining operation of a third embodiment of the electronic medical chart system of the present invention. The third embodiment is basically the same as the first and second embodiments. However, when the data of the electronic medical chart 150 is directly changed by the keyboard or the like, which is input means other than the electronic pen 200, selection is made whether to reflect the change in the paper medical chart 100. When the reflection is necessary, a reprint is made. When information not required to be reflected in the paper medical chart, information having low-importance, nursing care record or the like, is additionally entered in the electronic medical chart 150 with the input means other than the electronic pen 200, a reprint is not made.

First, in S300, the medical information is inputted in the electronic medical chart 150 with the input means (for example, medical chart input terminal) other than the electronic pen 200. Next, in S301, it is judged whether the inputted changing part is reflected in the paper medical chart 100. When it is judged the reflection is necessary, the succeeding procedures follow the processes of S104 and S105 shown in FIG. 9.

That is, in S104, the input means identifying part 404 notifies the medical chart ID identifying part 402 that the input means is not the digital pen 200, and the medical chart ID identifying part 402 makes the correlation between the inputted database and the medical chart ID invalid.

Next, in S105, the medical chart ID identifying part 402 issues the new medical chart ID to correlate the new medical chart ID with the database. In the medical chart printing terminal 700, the arrangement pattern based on the new ID and the recorded medical information are printed on the new medical chart form.

Figure 1:
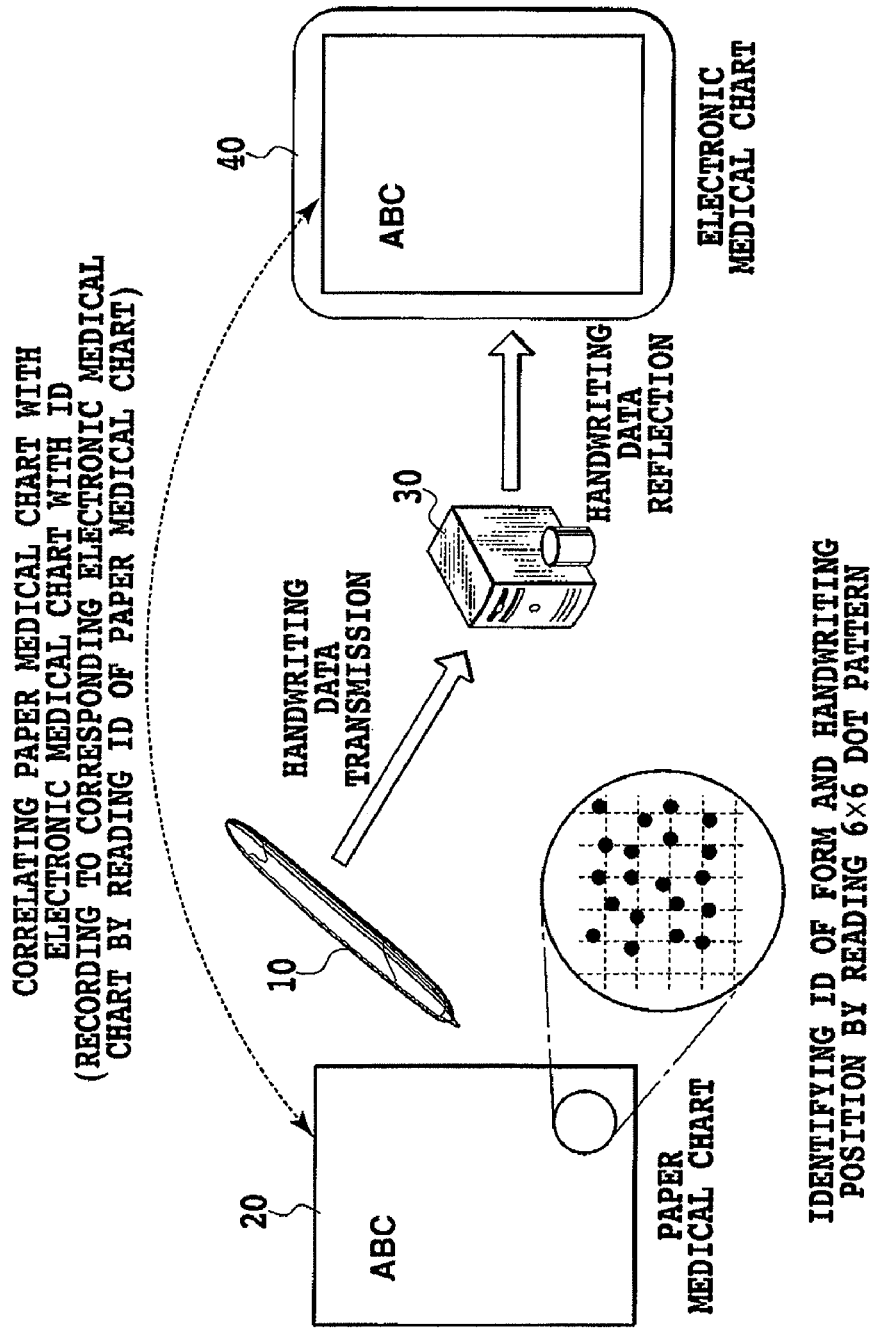
FIG. 1 is a schematic diagram of a conventional electronic medical chart system using an electronic pen.
Figure 2:
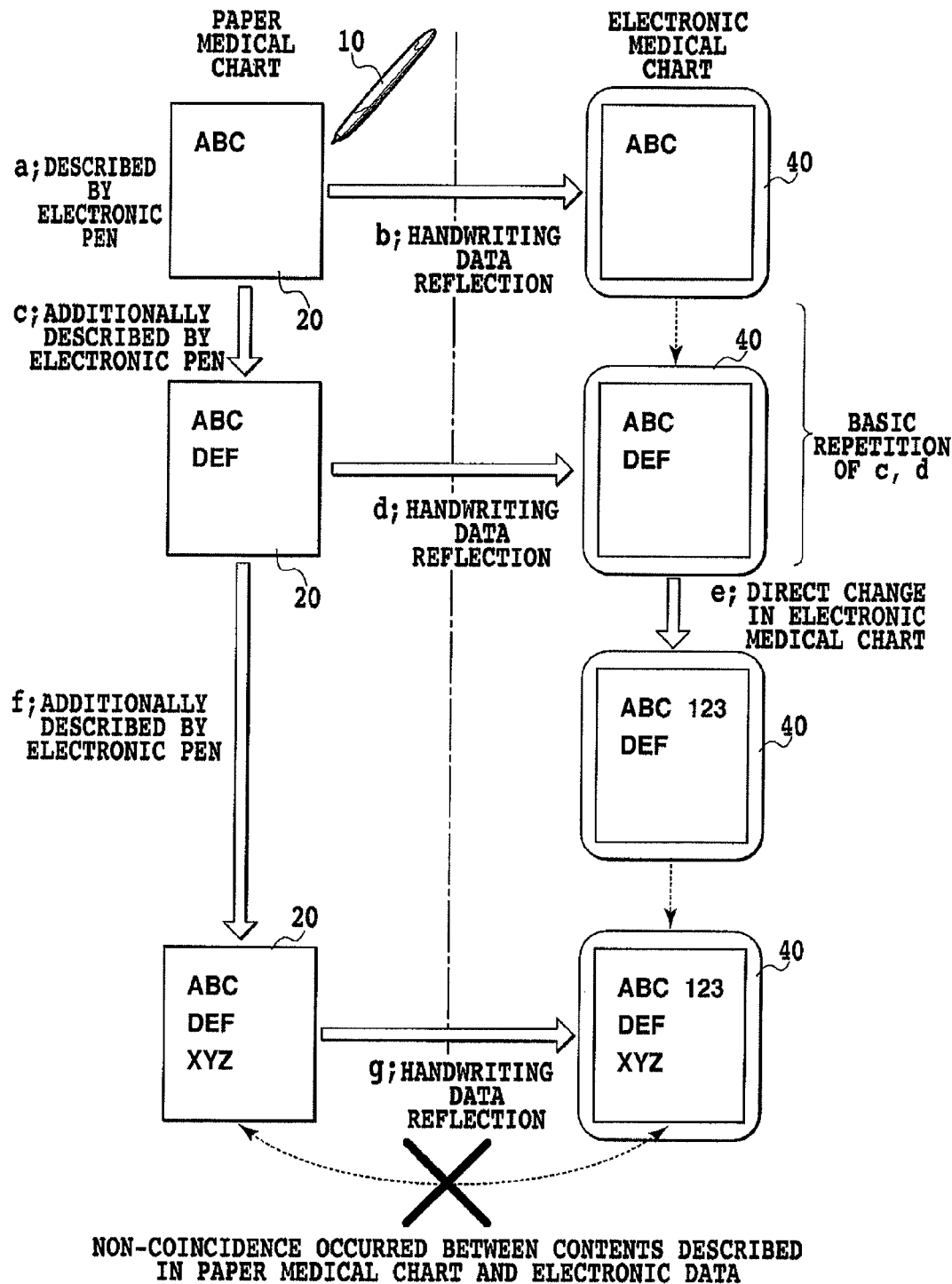
FIG. 2 is an explanatory diagram of operation of the conventional electronic medical chart system shown in FIG. 1.

The present invention is described above in detail based on the embodiments. However, the present invention is not limited to the above embodiments, and various modifications can be of course made without departing from the scope of the present invention. Additionally, although the electronic medical chart and paper medical chart are described as examples, the processing method shown in FIG. 2 or the like may be, as a matter of course, applied, with the electronic pen by substituting the medical chart input terminal with an electronic input terminal and substituting the electronic medical chart server with a database server, to the case of dealing with not only medical information such as a medical chart but also the other ordinary information.

Additionally, a recording medium can be employed in which a program for executing each step of the above method for data processing is recorded and which is readable by a computer.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-102289, filed Apr. 3, 2006, which is hereby incorporated by reference herein in its entirety.

What is claimed is:

1. An electronic medical chart system having at least one computer for maintaining a medical record, comprising:

entering unit configured enter the medical record on a medical chart having an ID assigned thereto to generate medical record data constituted by contents and positional coordinates of the entering, wherein the ID is composed of fine dots printed on the entire surface of a form in advance;

data management unit configured to maintain the medical record data;

data correlation unit configured to correlate the medical record data with a first medical chart having a first ID assigned thereto;

data control unit configured to control communication of the medical record data between the entering unit and data management unit;

data correlation release unit configured to release a correlation between the medical record data and the first medical chart having the first ID assigned thereto in a case where the medical record data is changed, to provide changed medical record data, by entering unit other than the entering unit for the first medical chart having the first ID assigned thereto;

display unit configured to, in a case where information is entered on the first medical chart having the first ID assigned thereto after the correlation between the medical record data and the first medical chart having the first ID assigned thereto is released by the data correlation release unit, recognize the first medical chart having the information entered thereon as being released by the data correlation release unit based on the first ID assigned to the first medical chart and display a dialogue for printing the changed medical record data;

medical chart print unit configured to print a second medical chart composed of the changed medical record data, wherein the second medical chart has a second ID different from the first ID assigned thereto; and reflecting unit configured to, in a case where the second medical chart is printed with the medical chart print unit and additional medical record is entered with the entering unit on the second medical chart having the second ID assigned thereto, identify the second ID and allow the medical record on the second medical chart to coincide with the medical record data maintained by the data management unit by having additional medical record entered on the second medical chart to be reflected in the medical record data maintained by the data management unit wherein at least one of the units is included in the at least one computer.

2. The electronic medical chart system according to claim 1, wherein the first medical chart comprises a communications instruction region for issuing an instruction on communication of the medical record data between the entering unit, data management unit and data control unit with a specific arrangement pattern of the fine dots.

3. The electronic medical chart system according to claim 2, further comprising:

further data management unit for warning a user that writing is not allowed and for requesting the user to print a second medical chart when the medical record is written in the first medical chart after the correlation between the first medical chart and medical record data is released by the data correlation release unit; and medical chart print unit for printing a new second medical chart.

4. The electronic medical chart system according to claim 2, further comprising user selection unit to release data correlation for allowing a user to select whether to release the correlation between the first medical chart and medical record data before the correlation between the first medical chart and medical record data is released when the medical record data is changed by entering unit other than the entering unit for the first medical chart.

5. The electronic medical chart system according to claim 2, wherein the entering unit comprises:

reading unit for recognizing the fine dots;

conversion unit for converting handwriting obtained by entering the medical record in the first medical chart and the positional coordinates into medical record data; and communications unit for performing communication of the medical record data between the data control unit and data management unit.

6. The electronic medical chart system according to claim 1, further comprising:

further data management unit for warning a user that writing is not allowed and for requesting the user to print a second medical chart when the medical record is written in the first medical chart after the correlation between the first medical chart and medical record data is released by the data correlation release unit; and medical chart print unit for printing a new second medical chart.

7. The electronic medical chart system according to claim 6, further comprising user selection unit to release data correlation for allowing the user to select whether to release the correlation between the first medical chart and medical record data before the correlation between the first medical chart and medical record data is released when the medical record data is changed by entering unit other than the by entering unit for the first medical chart.

8. The electronic medical chart system according to claim 6, wherein the entering unit comprises:

reading unit for recognizing the fine dots;

conversion unit for converting handwriting obtained by entering the medical record in the first medical chart and the positional coordinates into medical record data; and communications unit for performing transmission/reception of the medical record data between the data control means and data management unit.

9. The electronic medical chart system according to claim 1, further comprising medical chart print unit for printing a new second medical chart immediately after the correlation between the first medical chart and medical record data is released by the data correlation release unit.

10. The electronic medical chart system according to claim 9, further comprising user selection unit to release data correlation for allowing a user to select whether to release the correlation between the first medical chart and medical record data before the correlation between the first medical chart and medical record data is released when the medical record data is changed by entering unit other than the entering unit for the first medical chart.

11. The electronic medical chart system according to claim 9, wherein the entering unit comprises:

reading unit for recognizing the fine dots;

conversion unit for converting handwriting obtained by entering the medical record in the first medical chart and the positional coordinates into medical record data; and communications unit for performing communication of the medical record data between the data control unit and data management unit.

12. The electronic medical chart system according to claim 1, further comprising user selection unit to release data correlation for allowing a user to select whether to release the correlation between the first medical chart and medical record data before the correlation between the first medical chart and medical record data is released when the medical record data is changed by entering unit other than the entering unit for the first medical chart.

13. The electronic medical chart system according to claim 12, wherein the entering unit comprises:
reading unit for recognizing the fine dots;
conversion unit for converting handwriting obtained by entering the medical record in the first medical chart and the positional coordinates into medical record data; and
communications unit for performing communication of the medical record data between the data control unit and data management unit.

14. The electronic medical chart system according to claim 1, wherein the entering unit comprises:
reading unit or recognizing the fine dots;
conversion unit for converting handwriting obtained by entering the medical record in the first medical chart and the positional coordinates into medical record data; and
communications unit for performing communication of the medical record data between the data control unit and data management unit.

15. The electronic medical chart system according to claim 14, wherein the conversion unit is a processor and the processor performs image processing to an arrangement pattern of the fine dots recognized by the reading unit and has a function for calculating a current position of the entering unit.

16. The electronic medical chart system according to claim 15, wherein the processor compares images of the arrangement patterns of the fine dots recognized by the reading unit with each other, and has a function for calculating a movement direction and distance of the entering unit.

17. At least one apparatus for data processing by at least one computer, comprising:
receiving unit configured to receive first information that is entered on paper by an electronic pen, wherein the paper has an ID assigned thereto;
input unit configured to input second information being inputted with input other than the electronic pen; and
data management unit configured to maintain the first information received by the receiving unit and the second information inputted with the input unit;
data correlation unit configured to correlate the first information on the paper maintained by the data management unit with the second information inputted by the input unit;
data correlation release unit configured to, in a case where the second information maintained at the data management unit is changed by input using the input unit, release the correlation between the first information on the paper and the second information maintained at the data management unit,
display unit configured to, in a case where third information is entered on the paper after the correlation between the first information and the second information maintained at the data management unit is released by the data correlation unit, recognize the paper as being released by the data correlation release unit based on the first ID assigned to the paper and display a dialogue for printing the entered third information;
print unit configured to print paper having a second ID different from the first ID assigned thereto, the paper having the third information; and
reflecting unit configured to, in a case where fourth information is entered on the paper having the second ID assigned thereto, identify the second ID and allow the first information to coincide with the second information by having the fourth information entered on the paper having the third information to be reflected in the second information maintained by the data management unit,
wherein at least one of the units is included in the at least one computer.

18. A method for data processing in a data processing device having a computer processor, comprising the steps of:
receiving first information that is entered on paper by an electronic pen wherein the paper has an ID assigned thereto;
inputting second information that is inputted with input means other than the electronic pen;
managing data for maintaining the first information received in the receiving step and the second information inputted in the inputting step;
correlating data by correlating the first information on the paper maintained in the data managing step with the second information inputted in the inputting step;
releasing the correlation between the first information on the paper and the second information maintained in the data managing step, in a case where the second information maintained in the data managing step is changed by the input in the inputting step; and
in a case where third information is entered on the paper after the correlation between the first information and the second information is released in the releasing step, recognizing the paper as being released in the releasing step based on the first ID assigned to the paper and displaying a dialogue for printing the entered first additional information;
printing paper having a second ID different from the first ID assigned thereto, the paper having the third information; and
in a case where fourth information is entered on the paper having the second ID assigned thereto, identifying the second ID and allowing the first information to coincide with the second information by having the fourth information entered on the paper having the third information to be reflected in the second information maintained by the managing step,
wherein at least one of the steps is performed by the computer processor.

* * * * *